United States Patent [19]

Svensson

[11] Patent Number: 4,866,204

[45] Date of Patent: Sep. 12, 1989

[54] METHOD OF PREPARING SUBSTITUTED CYCLIC CARBOXYLIC ACIDS

[75] Inventor: Nils A. Svensson, Mölndal, Sweden

[73] Assignee: Nobel Chemicals AB, Karlskoga, Sweden

[21] Appl. No.: 156,036

[22] Filed: Feb. 16, 1988

[30] Foreign Application Priority Data

Feb. 18, 1987 [SE] Sweden ................................ 8700657

[51] Int. Cl.⁴ ............................................ C07C 51/265
[52] U.S. Cl. ..................................... 562/416; 502/152; 502/163; 502/170; 502/171; 562/412; 562/434; 562/435
[58] Field of Search ............... 562/412, 416, 417, 434, 562/435; 502/152, 163, 170, 171

[56] References Cited

U.S. PATENT DOCUMENTS 3,985,809 10/1976 Becking ........................ 562/411 X
4,423,245 12/1983 Lee ................................ 562/416

Primary Examiner—Werren B. Lone
Assistant Examiner—Vera C. Clarke
Attorney, Agent, or Firm—Dennison, Meserole, Pollack & Scheiner

[57] ABSTRACT

A method is disclosed for preparing a substituted cyclic carboxylic acid from a corresponding substituted cyclic hydrocarbon. The hydrocarbon is oxidized in oxygen or air in a liquid phase in an organic solvent under alkaline conditions, in the presence of a catalyst selected from the group consisting of metal tetraphenylporphins, metal acetylacetonates, metal phthalocyanines and mixtures thereof. The oxidation is capable of proceeding generally at room temperature and atmospheric pressure.

17 Claims, No Drawings

METHOD OF PREPARING SUBSTITUTED CYCLIC CARBOXYLIC ACIDS

This invention concerns a method of making substituted cyclic carboxylic acids by oxidation with air or oxygen in the presence of metal catalysts.

Substituted cyclic carboxylic acids are important intermediates for dyestuffs pharmaceuticals and other products. As examples of such products can be mentioned nitro- and chlorosubstituted benzoic acids, which are produced in a commercial scale by oxidation with nitric acid under pressure. Attempts to make these products by oxidation with air have so far met with great difficulties.

According to this invention such carboxylic acids can be prepared from the corresponding substituted hydrocarbons by oxidation with air or oxygen in a liquid phase at normal pressure using small amounts of metal catalysts of the type metal tetraphenylporphin. Remarkable high yields were obtained.

As a non-limiting example of the carrying out and the result of the method the preparation of o-nitrobenzoic acid from o-nitrotoluene will be described.

In a 250 ml 3-neck flask with a drop-in funnel and a pipe for gas intake 100 ml methyl alcohol and 34.0 g KOH was charged. The mixture was cooled to 25° C. and then 10 mg of recently prepared Fe (TPP) Cl (iron-tetraphenylporphin chloride) was added. 13.7 g of o-nitrotoluene was added and then a powerful passing through of air was started. After 18 hours the passing through of air was interrupted and 100 ml of $H_2O$ was added.

It is suitable to work up the product by filtration and extraction with ethyl acetate, acidifying of the water phase with conc. HCl and extraction with ethyl acetate, drying ($Na_2SO_4$) and evaporation, which will give pure o-nitrobenzoic acid by recrystallisation. The yield, determined by gas chromatography, was 95%.

The catalyst was prepared by refluxing tetraphenyl-porphin in dimethylformamide. Then two equivalents of $FeCl_2.4H_2O$ were added and the mixture was refluxed for some additional minutes. The mixture was cooled with an ice-bath and water was added. The crystals, that were formed, were filtered and were washed with water. The crystals were then dried in the air.

The method of the invention can also be used for the preparing p-nitrobenzoic acid, chloro- and chloronitrosubstituted benzoic acids and substituted phthalic acids and further products from the corresponding substituted hydrocarbons.

Other metal tetraphenylporphins can be used instead of or together with iron tetraphenylporphin chloride. The metal can for example be Ni, Mn or vanadium.

Other catalysts which can be used are metal acetyl acetonates in which the metal can be Ni, Cu, Co, Mn, Cr or Ti. It is also possible to use metal phthalocyanines as catalysts. Also combinations of these catalysts can be used.

The following examples will give a further illustration of the usefulness of the method for the synthesis of different substituted carboxylic acids.

The general procedure was the same as described above for the oxidation of o-nitrotoluene. After the passing through of air, adding of water and filtering, the water layer was extracted and acidified giving crystallized products, which were analyzed as crude carboxylic acids.

The following table shows the results of such experiments:

| Substituted Hydrocarbon | Catalyst | Crude Product |
|---|---|---|
| o-Nitrotoluene | Cu—phthalocyanine | o-Nitro-benzoic acid |
| " | Cu—PC(SO$_3$Et$_4$N)$_4$ | " |
| | Mn—tetraphenyl-porphin | |
| 2-Chloro-4-nitrotoluene | Cu—phthalocyanine | 2-Chloro-4-nitro-benzoic acid |
| " | Fe—tetraphenyl-porphin chloride | " |
| 4-Nitro-m-xylene | " | 4-Nitro-phthalic-acid |
| " | Cu—phthalocyanine | " |

The method can preferably be carried out with air at normal temperature and atmospheric pressure. In certain cases can however other temperatures be suitable as well as superatmospheric pressure in certain cases. Even if air is preferred as oxidation agent it is possible to use oxygen.

Using the method according to the invention nitrobenzoic acids, for example, can be produced in a very economical way in high yields and without large amounts of by-products.

As a solvent methyl alcohol has been used in the examples above but also other alcohols, such as ethyl alcohol can be used.

The oxidation is performed in alkaline solution. As examples both KOH and NaOH can be used as alkalis.

I claim:

1. Method for preparing a substituted cyclic carboxylic acid from a corresponding substituted cyclic hydrocarbon, comprising oxidizing in oxygen or air, said hydrocarbon in a liquid phase in an organic solvent under alkaline conditions, in the presence of a catalyst selected from the group consisting of Fe, Ni, Mn, and V tetraphenylporphins, Ni, Cu, Co, Mn, Cr, and Ti acetylacetonates, Ni, Cu, Co, Mn, Cr, and Ti phthalocyanines, and mixtures thereof.

2. Method according to claim 1, wherein Fe-tetraphenylporphin is used as said catalyst.

3. Method according to claim 1 wherein Mn-tetraphenylporphin is used as said catalyst.

4. Method according to claim 1, wherein a Cu-phthalocyanine is used as a catalyst.

5. Method according to claim 1, wherein methyl alcohol is used as said solvent.

6. Method according to claim 1 wherein o-nitrotoluene is oxidized to o-nitrobenzoic acid.

7. Method according to claim 1 wherein p-nitrotoluene is oxidized to p-nitrobenzoic acid.

8. Method according to claim 1 wherein a chloronitro-toluene is oxidized to the corresponding chloronitrobenzoic acid.

9. Method according to claim 1 wherein a nitroxylene is oxidized to the corresponding nitrophthalic acid.

10. Method according to claim 1, wherein the oxidation is carried out in alkaline solution containing KOH.

11. Method according to claim 1, wherein said catalyst is Ni or vanadium tetraphenylporphin.

12. Method according to claim 1, wherein said catalyst is selected from the group consisting of Ni, Cu, Co, Mn, Cr, and Ti-acetylacetonates, and mixtures thereof.

13. Method according to claim 1, wherein said oxidation is carried out at about 25° C. under atmospheric pressure.

14. Method according to claim 1, wherein said acid is a substituted benzoic or phthalic acid.

15. Method according to claim 14, wherein said acid is nitro-, chloro-, or chloronitro-substituted.

16. Method according to claim 1, wherein said solvent is an alcohol.

17. Method for preparing a substituted cyclic carboxylic acid from a corresponding substituted cyclic hydrocarbon, comprising oxidizing in oxygen or air, said hydrocarbon in a liquid phase in an alcohol solvent under alkaline conditions, in the presence of a catalyst selected from the group consisting of Fe, Ni, Mn and V tetraphenylporphins, Ni, Cu, Co, Mn, Cr and Ti acetylacetonates, Ni, Cu, Co, Mn, Cr, and Ti phthalocyanines, and mixtures thereof, said oxidizing being capable of proceeding at generally room temperature and atmospheric pressure.

* * * * *